(12) United States Patent
Baum et al.

(10) Patent No.: US 6,348,067 B1
(45) Date of Patent: *Feb. 19, 2002

(54) METHOD AND SYSTEM WITH SHAPE MEMORY HEATING APPARATUS FOR TEMPORARILY SUPPORTING A TUBULAR ORGAN

(75) Inventors: Abraham Baum, Givataim; Elisha Hoch, Rehovot; Israel Schnitzer, Tel-Aviv; Lior Kacir, Rehovot; Felix Rabinovich, Rishon Lezion; Reuben Ilia, Beersheva, all of (IL)

(73) Assignee: Israel Aircraft Industries Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/199,556

(22) Filed: Nov. 25, 1998

(51) Int. Cl.$^7$ .................................................. A61F 2/06
(52) U.S. Cl. ........................ 623/1.19; 606/191; 606/194
(58) Field of Search ................................ 606/190, 191, 606/194, 198, 23–31, 200, 78; 623/11–12, 1, 1.19, 1.18, 1.15, 1.3; 604/104, 280, 281, 282, 105, 283, 531, 264, 532; 608/198

(56) References Cited

U.S. PATENT DOCUMENTS

| 5,071,407 | A | * | 12/1991 | Termin et al. ............... 604/104 |
| 5,147,370 | A | * | 9/1992 | McNamara et al. ......... 606/108 |
| 5,562,641 | A | * | 10/1992 | Flomenbilt et al. .......... 606/198 |
| 5,407,432 | A | * | 4/1995 | Solar ............................ 604/164 |
| 5,441,516 | A | * | 8/1995 | Wang et al. ................. 606/198 |
| 5,503,636 | A | * | 4/1996 | Schmitt et al. .............. 606/200 |
| 5,523,092 | A | * | 6/1996 | Hanson et al. ................. 604/96 |
| 5,976,152 | A | * | 11/1999 | Regan et al. ................ 606/108 |

* cited by examiner

*Primary Examiner*—Henry J. Recla
*Assistant Examiner*—Vy Q. Bui
(74) *Attorney, Agent, or Firm*—Paul J. Sutton

(57) ABSTRACT

There is provided a system for opening and temporarily supporting a section of a generally tubular organ. The system includes a dilation catheter which has an integrally connected shape memory catheter tip. The shape memory catheter tip is made of a shape memory alloy. The shape memory catheter tip assumes a first shape at a first temperature and a second shape at a second temperature. Accordingly, the shape memory catheter tip is inserted into the body of the patient, while being in a narrow shape and expands within the body of the patient.

30 Claims, 13 Drawing Sheets

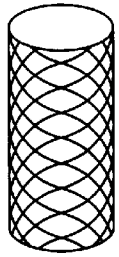
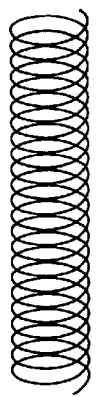
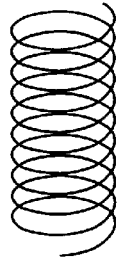
FIG.1A  
PRIOR ART
FIG.1B  
PRIOR ART
FIG.1C  
PRIOR ART
FIG.1D  
PRIOR ART
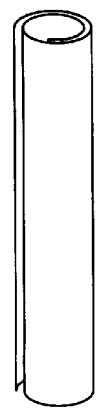
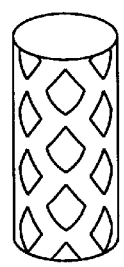
FIG.1E  
PRIOR ART
FIG.1F  
PRIOR ART
FIG.1G  
PRIOR ART
FIG.1H  
PRIOR ART

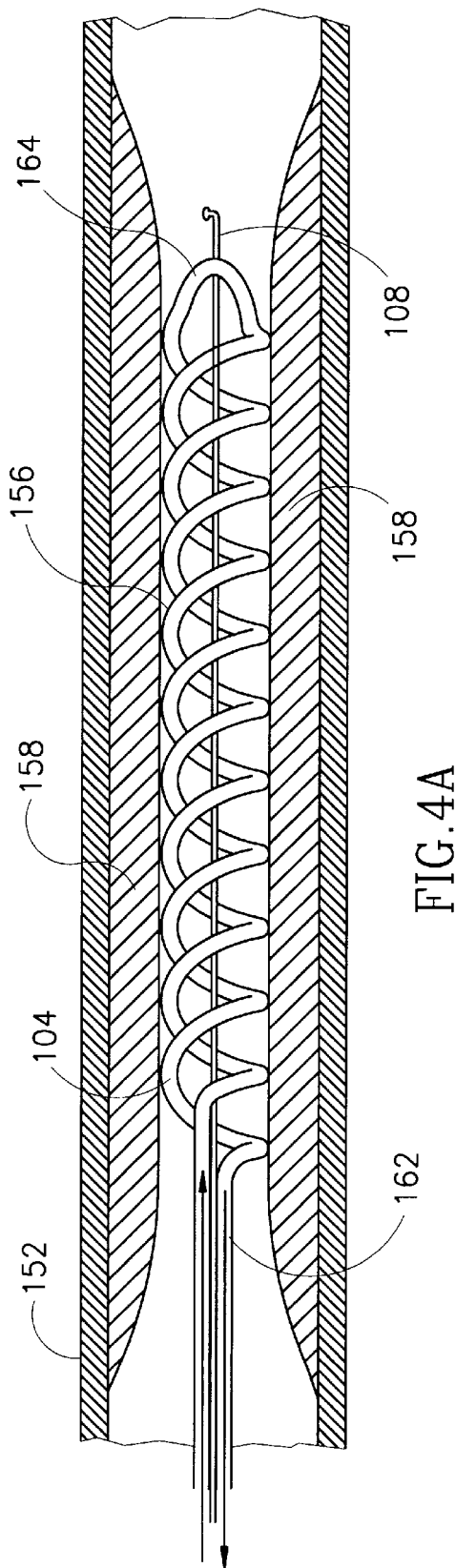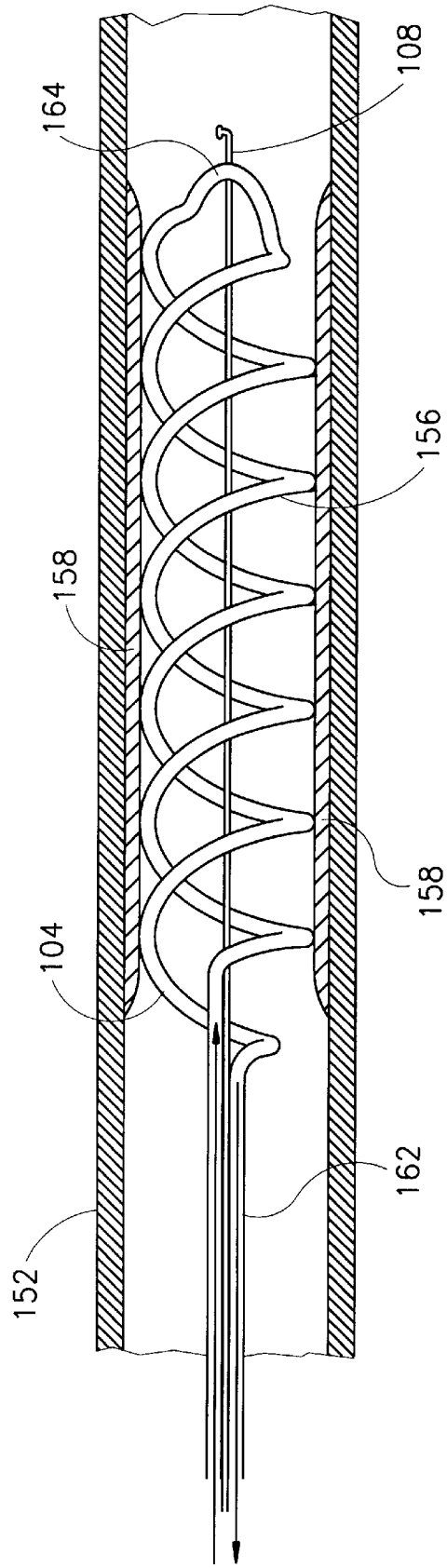
FIG.4A
FIG.4B

METHOD AND SYSTEM WITH SHAPE MEMORY HEATING APPARATUS FOR TEMPORARILY SUPPORTING A TUBULAR ORGAN

This application is a parent case of patent application Ser. No. 09/274,851.

FIELD OF THE INVENTION

The present invention relates to a method and a device for widening tubular organs in general and to a method and a device for widening arteries in particular.

BACKGROUND OF THE INVENTION

Devices and methods for widening tube shaped organs, in general and in the human body, in particular, are known in the art.

U.S. Pat. No. 5,716,410, to Wang et al, is directed to a catheter for vascular use. The catheter includes a directing mechanism and an inflatable balloon at the tip. The tip also includes a temporary stent, made of thermoplastic material. The catheter is inserted into the body of the patient, via a wide surface artery and the operator directs the catheter toward the destination location. When the tip is positioned at the destination location, then the operator pumps fluid to the balloon, via a tube, running along the catheter and starts inflating the balloon.

Reference is now made to FIG. 2, provided by Wang et al as FIG. 1, which is an illustration of a catheter, known in the art.

At the same time, the thermoplastic stent is heated, thereby unlocking its shape. The balloon, as it inflates, applies circumferencial pressure on the stent and the tubular organ, thereby forcing them to extend. Accordingly, the circumference of the tubular organ becomes larger. When the balloon brings the thermoplastic stent to the destination diameter, then the thermoplastic stent is cooled, thereby fixing its shape at a larger diameter, where it supports the tubular organ at an enlarged position.

Then, the operator, reduces the pressure within the balloon, which in turn deflates and becomes smaller than the enlarged circumference of the tubular organ. The thermoplastic stent is then kept within the tubular organ for a time period which may range from a few minutes to as long as a week. Finally, the thermoplastic stent is reheated, thereby unlocking its shape, and enabling its removal from the body of the patient.

It will be appreciated by those skilled in the art, that a balloon is often longer than the segment to be treated. Hence, the inflatable portion of the balloon extends beyond the desired segments to healthy segments, and can cause damage thereto.

Furthermore, when a balloon is inflated inside a blood vessel, it occludes the blood flow distally and becomes a full barrier for any blood flow therein. It will be appreciated by those skilled in the art that many blood vessel related balloon treatments are performed in coronary arteries. Accordingly, such a procedure, while blocking blood flow through the treated blood vessel, may cause ischemia or even cardiac arrest.

The balloon blocks the blood flow both in the axial (through the blood vessel) and radial directions blocking branches.

The complete obstruction, a balloon related treatment is usually limited to one or two minutes of inflation, since the patient can not tolerate long time inflations, because of severe pain and chest discomfort, due to ischemia.

It will be appreciated by those skilled in the art that a blood vessel is generally a flexible organ. This fact, combined with the short time period in which a balloon expands the circumference of the blood vessel, (as much as 40% of the cases) causes the balloon treated blood vessel to assume its original size (recoil) immediately, or within few months shortly after the treatment.

A stent is generally an element which is inserted into the tubular organ with the aid of a catheter. The initial shape of a stent is of an elongated cylinder, having a diameter which is smaller than the narrowed section of the tubular organ, through which it has to pass. At the beginning of the treatment, the stent is positioned in the stenosed segment.

Then, the circumference of the stent is widened, by various methods, known in the art. One of these methods includes inserting a balloon into the stent and applying pressure by inflating it therewith. Accordingly, the stent widens, thereby applying pressure on the narrowed blood vessel. As a result, the stent widens the cross section of the diseased segment.

Finally, the balloon is deflated and is removed from the stent, which remains in its widened position, forcing the widened blood vessel to remain at its new state. Afterwards, the stent is covered by local tissue and is anchored thereto. This poses a disadvantage in the usage of a stent since such a stent can not be removed. A stent is an alien element within a living organism, which might produce thrombus in it.

In many cases (15%–40%) instant stenosis occurs. The mechanism of this narrowing is intimal proliferation thereby causing a new blockage at the same location. It is known by those skilled in the art that sometimes, such a reoccurring blockage is difficult to treat and in some cases, surgery is needed, to remove and replace the clogged section.

In some instances the stent may be lost and migrate distally in the coronary artery, or sometimes in the aorta and its branches. The stent also can be stucked.

Shape memory effect (SME) is a phenomena, in shape memory alloys (SMA) of a reversible transition from one solid phase into the other (i.e., from Martensite into Austenite or from Austenite to Martensite). Heating the alloy causes the transition from Martensite into Austenite. Cooling the alloy causes the reverse transition, from Austenite into Martensite. NiTi alloys are examples for such shape memory alloys.

Martensite and Austenite are two solid state phases, which are typical for alloys. Each of these phases is characterized in a certain crystaline structure.

Basically there are two types of shape memory effects. The first type is called the one way shape memory effect (OWSM), where the material transits from one of the above phase states to the other, only once. The second type is called the two way shape memory effect (TWSM), where the material transits from one of the phase states to the other and back in a reversible process.

Shape memory alloys, such as Ni—Ti, Ni—Ti—X, Cu—Ni—Al, Cu—Zn—Al, Fe—Mn—Si, Ni—Ti—Co, Ni—Cu—X, Ni—Al and the like, are known in the art. These alloys exhibit a shape memory effect. In the martensite condition, the shape alloy material is relatively flexible and soft, and can be easily deformed. When the material undergoes the transition into an austenite state, it becomes more rigid, and is able to apply force and generate work, deform and enlarge the cross section of the blood vessel.

U.S. Pat. No. 5,540,713 to Shnepp-Pesch et al, is directed to an apparatus for widening a stenosis in a body cavity, also known as a shape memory stent. Shnepp-Pesch describes a stent made from a shape memory alloy, assuming a first predetermined shape at a first predetermined temperature and second predetermined shape at a second predetermined temperature. When heated from the first temperature to the second one, the shape memory stent changes its shape from a narrow generally cylindrical shape to a wider generally cylindrical shape.

Shnepp-Pesch describe a plurality of shapes which are applicable as shape memory stents. Reference is now made to FIGS. 1A–1H, provided by Shnepp-Pesch et al, as FIGS. 1A, 1B, 2A, 2B, 3A, 3B, 4A and 4B, respectively. These figures describe four shape memory stent structures, each at two states, one narrowed and the other enlarged.

It will be appreciated by those skilled in the art that this stent basically suffers the same disadvantages as any other stent, known in the art, as listed above.

SUMMARY OF THE PRESENT INVENTION

It is an object of the present invention to provide a system for opening and temporarily supporting generally tubular organs, in general and arteries in particular.

It is a further object of the present invention to provide a novel method for temporarily supporting a tubular organ, in general and vascular organs in particular.

In accordance with the present invention, there is thus provided a system for opening and temporarily supporting a section of a generally tubular organ. The system includes a dilation catheter which has an integrally connected shape memory catheter tip. The shape memory catheter tip is made of a shape memory alloy. The shape memory catheter tip assumes a first shape at a first temperature and a second shape at a second temperature. Accordingly, the shape memory catheter tip is inserted into the body of the patient, while being in a narrow shape and expands within the body of the patient.

According to one aspect of the invention, the shape memory catheter tip is generally hollow, thereby enabling flow of bodily fluid therethrough. It is noted that the flow of fluid can be performed both in a radial direction as well as in an axial direction.

The system can further include an energy control unit, connected to the dilation catheter, for controlling the temperature of the shape memory catheter tip and an energy transfer unit. The energy transfer unit is connected between the shape memory catheter tip and the energy control unit. It is generally located within the dilating catheter and transfers energy between the energy control unit and the catheter tip. According to one aspect of the invention, the energy transfer unit is connected to the shape memory catheter tip, thereby transferring energy to and from. According to another aspect of the invention, the energy transfer unit is not integrally connected to the shape memory catheter tip, thereby transferring energy to and from the vicinity of the catheter tip.

The shape memory catheter tip can include a generally cylindrical coil.

According to a further aspect of the invention, the first shape is generally the shape of a cylindrical coil having a first diameter and the second shape is generally the shape of a cylindrical coil having a second diameter. Hence, when the shape memory catheter tip transforms from the first shape to the second shape, it widens the organ, which is attached thereto, for example, an artery.

According to one aspect of the invention, the generally cylindrical coil has a solid cross section. According to one aspect of the invention, the generally cylindrical coil has a hollow cross section and hence, enables the flow of fluid therethrough.

It is noted that the generally cylindrical coil can have a cross section, which is selected from the list consisting of radial cross section, elliptical cross section, semi radial cross section, semi elliptical cross section, a near rectangular cross section and the like.

The energy transfer means can include a conduit or a plurality of conduits and the temperature control unit can accordingly include means for providing temperature controlled fluid towards the shape memory unit via the energy transfer means.

According to one aspect of the invention, the one of the conduits, is opened in the vicinity of the shape memory catheter tip, thereby releasing temperature controlled fluid in the vicinity of the shape memory catheter tip.

According to a further aspect of the invention, the shape memory catheter tip includes a generally cylindrical coil, having a hollow cross section, through which temperature controlled fluid can flow.

According to one aspect of the invention, the cylindrical coil is connected to one of the conduits at a first end, and is open at a second end. Hence the conduit transfers temperature controlled fluid to the shape memory catheter tip, via the first end, and the shape memory catheter tip releases the temperature controlled fluid via the second end.

According to another aspect of the invention, the cylindrical coil is connected to a first one of the conduits at a first end thereof, and to a second one of the conduits, at the second end thereof. Hence the first conduit transfers temperature controlled fluid to the shape memory catheter tip, via the first end, and the second conduit receives temperature controlled fluid from the shape memory catheter tip, via the second end.

It is noted that the temperature control unit can include a power supply unit, which is electrically connected to the shape memory unit, thereby electrically heating the shape memory unit from the first temperature to the second temperature. Accordingly, the energy transfer means can include an electricity conducting unit, such as electrical wires, which are electrically connected to the shape memory unit.

The shape memory alloy, used to manufacture the shape memory catheter tip can be selected from the list consisting of: Ni—Ti, Ni—Ti—X, Cu—Ni—Al, Cu—Zn—Al, Fe—Mn—Si, Ni—Ti—Co, Ni—Cu—X, Ni—Al and the like.

It is noted that the shape memory catheter tip can be characterized to operate at a plurality of temperatures. Accordingly, the first temperature is equal or below the temperature of the environment, in which the shape memory catheter tip is placed.

Alternatively the first temperature can be in the range of 38 degrees Celsius and 65 degrees Celsius or in the range of 42 degrees Celsius and 50 degrees Celsius. Similarly, the second temperature can be in the range of 5 degrees Celsius and 35 degrees Celsius or in the range of 20 degrees Celsius and 32 degrees Celsius. It is noted in the manufacturing process, the first and second temperatures can be swapped (i.e., the first temperature is lower than the second temperature).

In accordance with a further aspect of the present invention, the system further includes elastic means, such as a spring, which are attached to the shape memory catheter tip having an initial shape. The initial shape is generally similar to the first shape of the shape memory catheter tip. The elastic means apply force on the shape memory catheter tip so as to deform the shape memory catheter tip to the initial shape of the elastic means.

According to one aspect, where the shape memory catheter tip is made of a hollow cross section tube, the elastic means can be inserted within the shape memory unit. According to another aspect of the invention, the elastic means are attached to the shape memory unit, on the outside.

It is noted that the front section of the shape memory catheter tip can be shaped as a guiding front end.

Alternatively, the system according to the invention can further include a guiding unit having a guiding tip, wherein the guiding unit is located within the dilation catheter and the guiding tip extends beyond the shape memory catheter tip. Accordingly, the guiding tip is operable to move relative to the shape memory catheter tip.

It is noted that the first diameter can be smaller than the second diameter. Alternatively, the first diameter can be larger than the second diameter.

The shape of the shape memory catheter tip in the martensite state can be narrow with respect to the shape of the shape memory catheter tip in the austenite state. Alternatively, the shape of the shape memory catheter tip in the martensite state can be wider with respect to the shape of the shape memory catheter tip in the austenite state. With reference to the above elastic means, the initial shape assumes a shape which is similar to the shape of the shape memory catheter tip in the martensite state, and hence can be narrow or wide, respectively.

It is noted that the conduits which are connected to the catheter tip can be concentric or side by side.

BRIEF DESCRIPTION OF THE DRAWINGS

The present invention will be understood and appreciated more fully from the following detailed description taken in conjunction with the drawings in which:

FIGS. 1A–1H, are schematic illustrations of a tubular restraining devices, which are known in the art;

FIGS. 4A and 4B are illustrations of the tip end of the device of FIG. 3, constructed and operative in accordance with another preferred embodiment of the present invention;

DETAILED DESCRIPTION OF PREFERRED EMBODIMENTS

The present invention overcomes the disadvantages of the prior art by providing a novel device which is a catheter, having a hollow SMA element as its tip.

Furthermore, the present invention provides a novel method for operating the device of the invention, which overcomes the disadvantages of the prior art.

Figure 2:
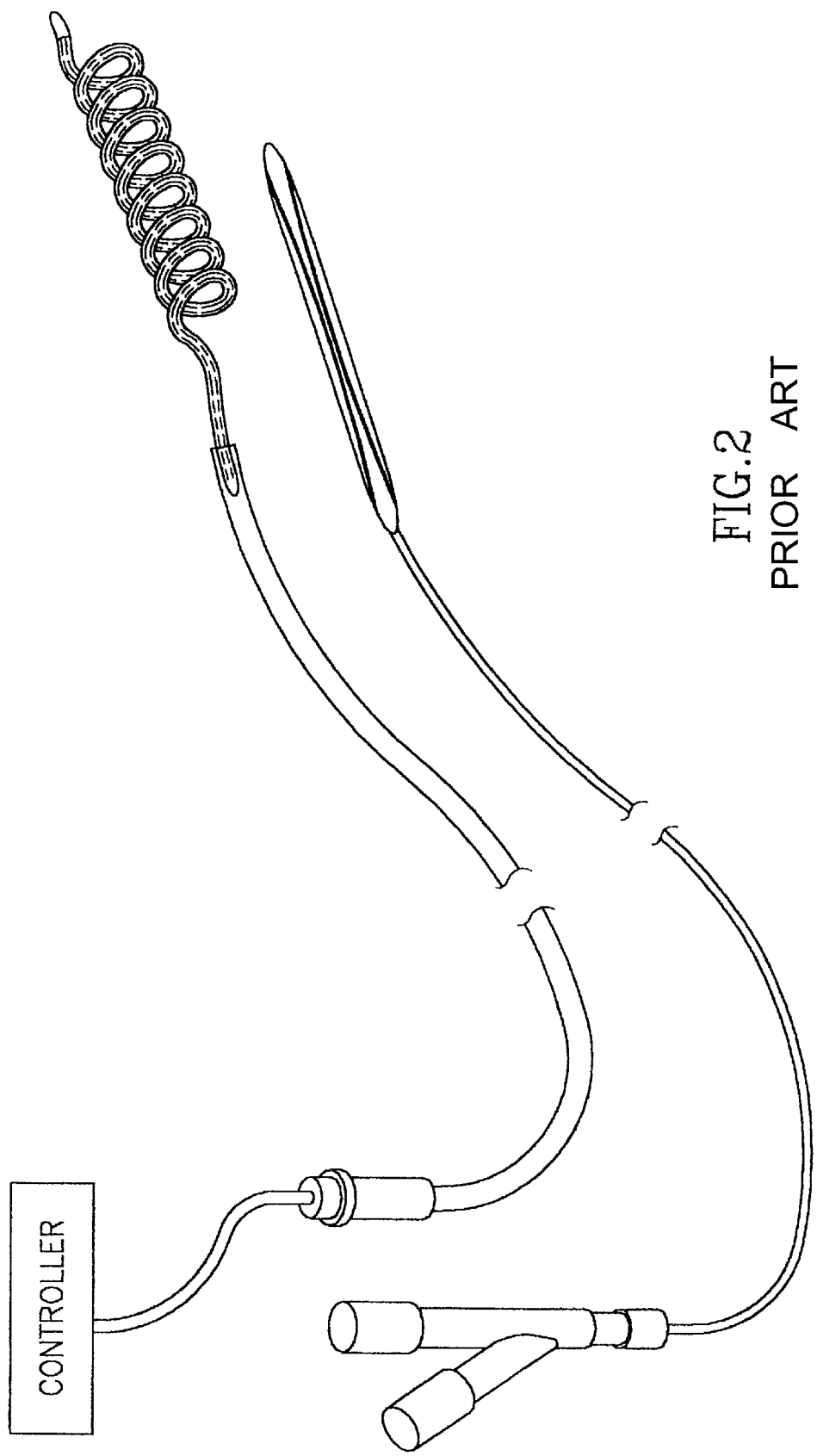
FIG. 2 is a schematic illustration of a catheter having a balloon as its tip, which is known in the art.
Figure 3:
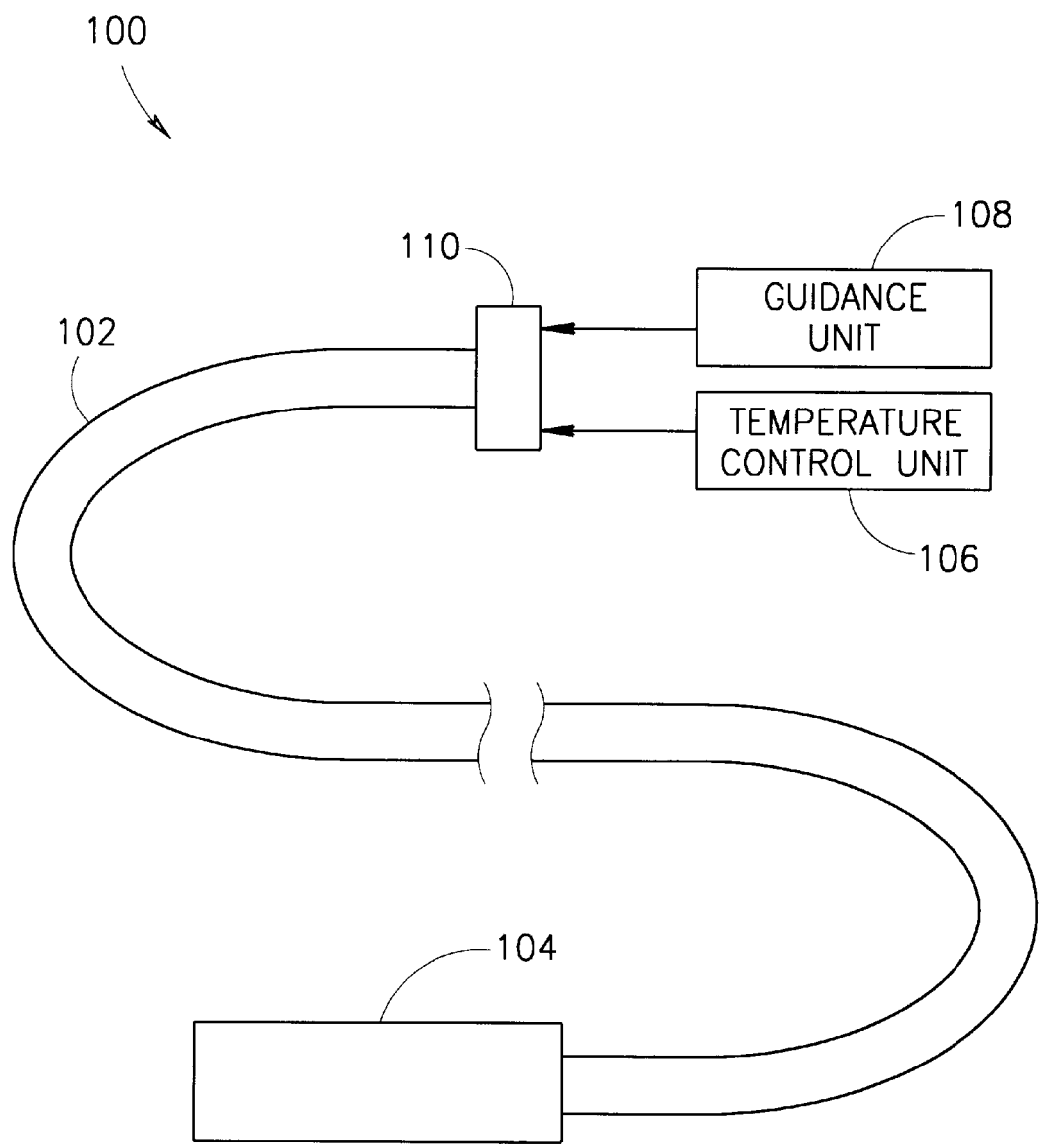
FIG. 3 is a schematic illustration of a device for treating a tubular organ, constructed and operative in accordance with a preferred embodiment of the invention.

Reference is now made to FIG. 3 which is a schematic illustration of a device, generally referenced 100, for treating a tubular organ, constructed and operative in accordance with a preferred embodiment of the invention.

The device 100 includes a guiding catheter 102, a "Y" connector 110, a hollow SMA tip 104, a guidance unit 108 and a fluid supply and temperature control unit 106.

The guide wire 108 is inserted through guiding catheter 102 via the "Y" connector 110. The temperature control unit is connected to the Hollow SMA tip which is inserted via the "Y" connector 110 and over the guide wire 108.

The guiding catheter 102 is an elongated tubular element which guides and locates the tip 104 within the patients tubular organ, which for example, can be a blood vessel, a urether, urethra, bile duct, colon eosophagus, stenosed valve, etc. and the like. The user of the device 100, which is a medically trained person, uses the guidance Wire 108 to insert over it SMA tip into the diseased segment.

Reference is also made now to FIGS. 4A and 4B, which are illustrations of the tip end of the device 100, of FIG. 3. FIG. 4A shows the tip 104 inserted into a blood vessel 152, having a section 158, which is relatively narrower than the rest of the blood vessel.

The tip 104 includes a hollow shaped SMA element which is adapted to perform a transition from one shape at a first predetermined temperature range to another shape, at a second predetermined temperature range.

In the present example, the tip includes a helical SMA element 156. The helical SMA element 156 has a narrow circumference shape at a temperature, which is equal or lower to a first temperature value $T_1$, as shown in FIG. 4A. The helical SMA element 156 has a wide cross section shape at a temperature, which is equal or higher to a second temperature value $T_2$, as shown in FIG. 4B.

The helical SMA element 156 is inserted over the guide wire 108 through guiding catheter 102 (FIG. 3). It is shaped so that its front end 164 (FIG. 4) has a round shape which is designed so that no damage is inflicted onto the blood vessel through which the tip is inserted. At its other end 162, the helical SMA element 156 is connected to hollow tubes, which are able to supply various fluid temperatures thereon (shown in detail in conjunction with FIG. 8).

The device 100 is used to expand the circumference of the blood vessel 152, at its narrowed cross section 158, using the SMA tip 104.

Accordingly, the user inserts the SMA element 156 into the blood vessel 152 and positions it in the diseased segment 158. It is noted that all through the insertion phase, the helical SMA element 156 is maintained at a temperature, which is not higher than $T_1$, thereby assuming its narrowed form.

When the helical SMA element 156 is located within the diseased section 158, then, the user operates the temperature control unit 106, which heats the helical SMA element 156 to a temperature which is not lower than $T_2$. As the helical SMA element 156 heats, it undergoes a transition from its narrow shape into its wider shape. Accordingly, the helical SMA element 156 applies circumferencial pressure on the diseased segment 158, thereby forcing it to become wider (FIG. 4B).

According to the present invention, the user can maintain the helical SMA element 156 at its position, for a considerable period of time, which is in the order of minutes, hours and days, as needed.

As the shape of the helical SMA element 156 does not block flow. No ischemia is produced and hence, no harm or suffer is inflicted onto the patient, during this time period.

After reducing the SMA element 156 to its' original size, the physician can direct it to another location, within the artery and use it again. Accordingly, the device of the present invention can be used for a plurality of narrowed artery locations, one after the other, without the need to remove the catheter out of the patients body.

According to the present invention, the heating up and cooling down of the helical SMA element 156 can be performed in a plurality of ways such as inducing a temperature bearing fluid there through, electric current, radiation, induction heating, and the like.

According to one aspect of the present invention, the helical SMA element 156 is made of a hollow wire, through which temperature bearing fluid is induced or others.

As the diseased segment 158 is forced to be in a widened state (FIG. 4B) for a considerable time, by the helical SMA element 156, then the probability of it shrinking back to its narrow state (FIG. 4A) decreases significantly.

At the end of the treatment, the user, operates the temperature control unit 106, to lower the temperature of the helical SMA element 156, which in turn returns to its initial state as shown in FIG. 4A. Finally, the user takes out the SMA catheter 100 than the guide wire 108 and finally the guiding catheter 102 out of the patients body, or to another vessel which needs to be dilated.

It will be noted that according to this aspect of the present invention, no element such as a stent, remains in the artery, to maintain its widened state, at the end of the treatment. Hence, at any time after the treatment, any type of catheter can be inserted into the artery, passing distally through section 158, for example, for repeating the treatment of section 158.

According to the present invention, the helical SMA element 156 is made of a hollow conduit. A fluid flowing there through having a predetermined temperature, applies that temperature thereon. Accordingly, a temperature change can be applied on the element 156.

The side walls of the catheter are substantially round shaped having a smooth surface, for reducing the probability of inflicting any damage to the inside walls of the treated artery (the intima).

Reference is now made to FIGS. 5A, 5B, 5C, 5D and 5E, which are illustrations of cross sectional variations for helical SMA element 156, constructed and operative in accordance with the present invention.

Figure 5A:
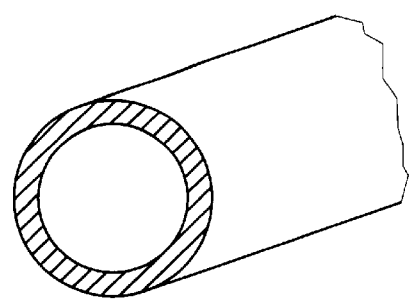
FIGS. 5A, 5B, 5C, 5D and 5E are illustrations of typical cross sectional variations for helical SMA element of FIGS. 4A and 4B.
Figure 5B:
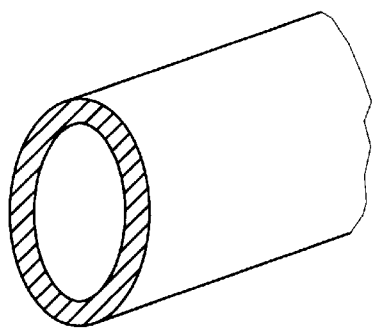
Figure 5C:
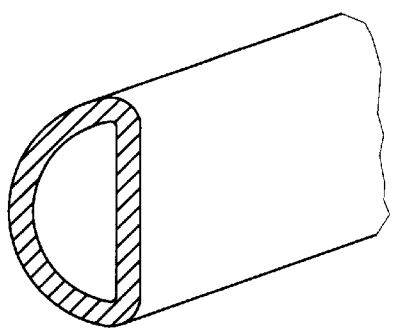
Figure 5D:
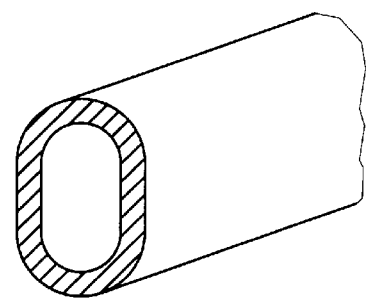
Figure 5E:
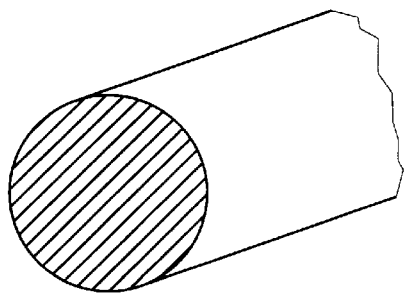

FIG. 5A shows a circular cross section, FIG. 5B shows an elliptical cross section, FIG. 5C shows a half elliptical cross section, FIG. 5D shows a near rectangle cross section and FIG. 5E shows a solid (full) radial cross section.

Figure 6:
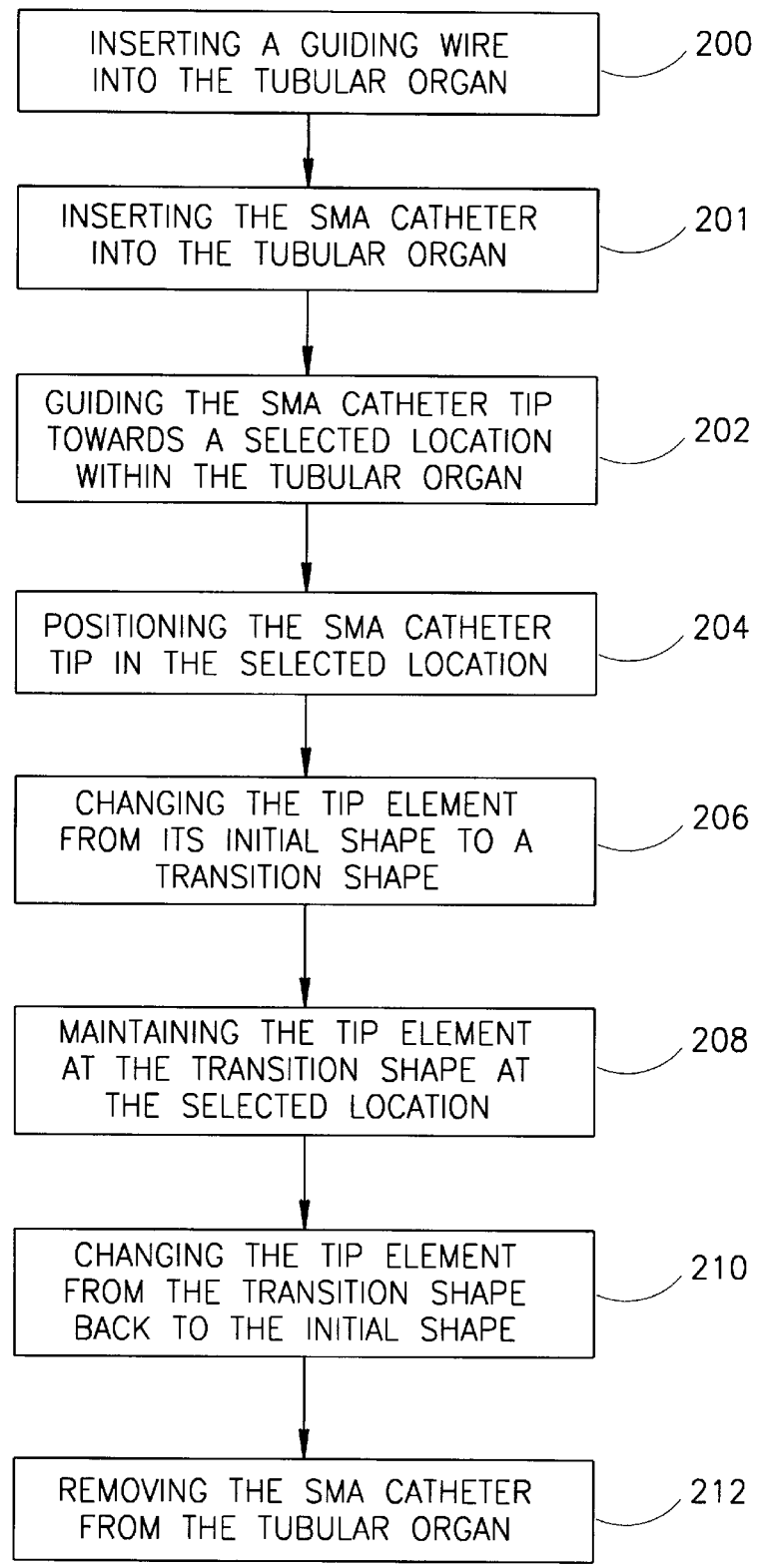
FIG. 6 is a schematic illustration of a method for operating the device of FIG. 3, operative in accordance with another preferred embodiment of the present invention.

Reference is now made to FIG. 6, which is a schematic illustration of a method for operating the device 100 of FIG. 3, operative in accordance with another preferred embodiment of the present invention.

In step 200, a guiding wire is inserted into the tubular organ within the body of the patient, and is guided into the section to be treated. This tubular organ can be, for example, a blood vessel, a urether, a urethra, bile duct, colon, eosophagus, stenosed valve, and the like. In the case of a blood vessel, the guiding tip can be inserted from a peripheral artery.

In step 201, the device 100, which is an SMA catheter is inserted into the tubular organ, guided via the guiding wire towards the section to be treated.

In step 202, the device 100 is guided through the tubular organ towards a selected location, which is a portion of the tubular organ which is narrower than as it should be and need to be widened. In the present example, there is a blockage in this location caused by atherosclerosis.

In step 204, the user, which is part of the medical stuff treating the patient, positions the tip of the SMA catheter in the selected location. The SMA element can be heated by fluid, electric current, radiation, induction heating, and the like.

In step 206, the SMA tip of the device 100 changes from an initial shape to a transition shape. This can be done by means of a phase transition which can be caused by a temperature change (increase). Being in the transition shape, the SMA tip applies circumferencial pressure on the walls of the selected section, thereby forcing it to increase its circumference (208). The tip is maintained in this position and shape, so as to reduce the probability of the selected section returning to its original circumference shortly after the treatment is ended.

In step 210, the tip element is changed from the transition shape back into the initial shape. This is done by means of a phase transition which is caused by a temperature change (decrease).

In step 212, the device 100 is removed from the tubular organ. It will be noted that the device 100, can remain in the body of the patient for a subsequent treatment of another such section.

It is noted that according to the present invention blood flow is maintained throughout the treatment and the device, according to the invention, does not block blood flow neither in the axial direction, nor in the radial direction. Accordingly, the method of the present invention is applicable for patients which may not endure a blood blocking balloon treatment.

Since the device of the present invention is completely removed from the body of the patient and leaves no object therein, then, the probability of intimal proliferation in the treated segment, is significantly reduced.

It is noted that the method of the present invention enables the physician to treat conical shaped segment by using conical SMA tip.

Figure 7:
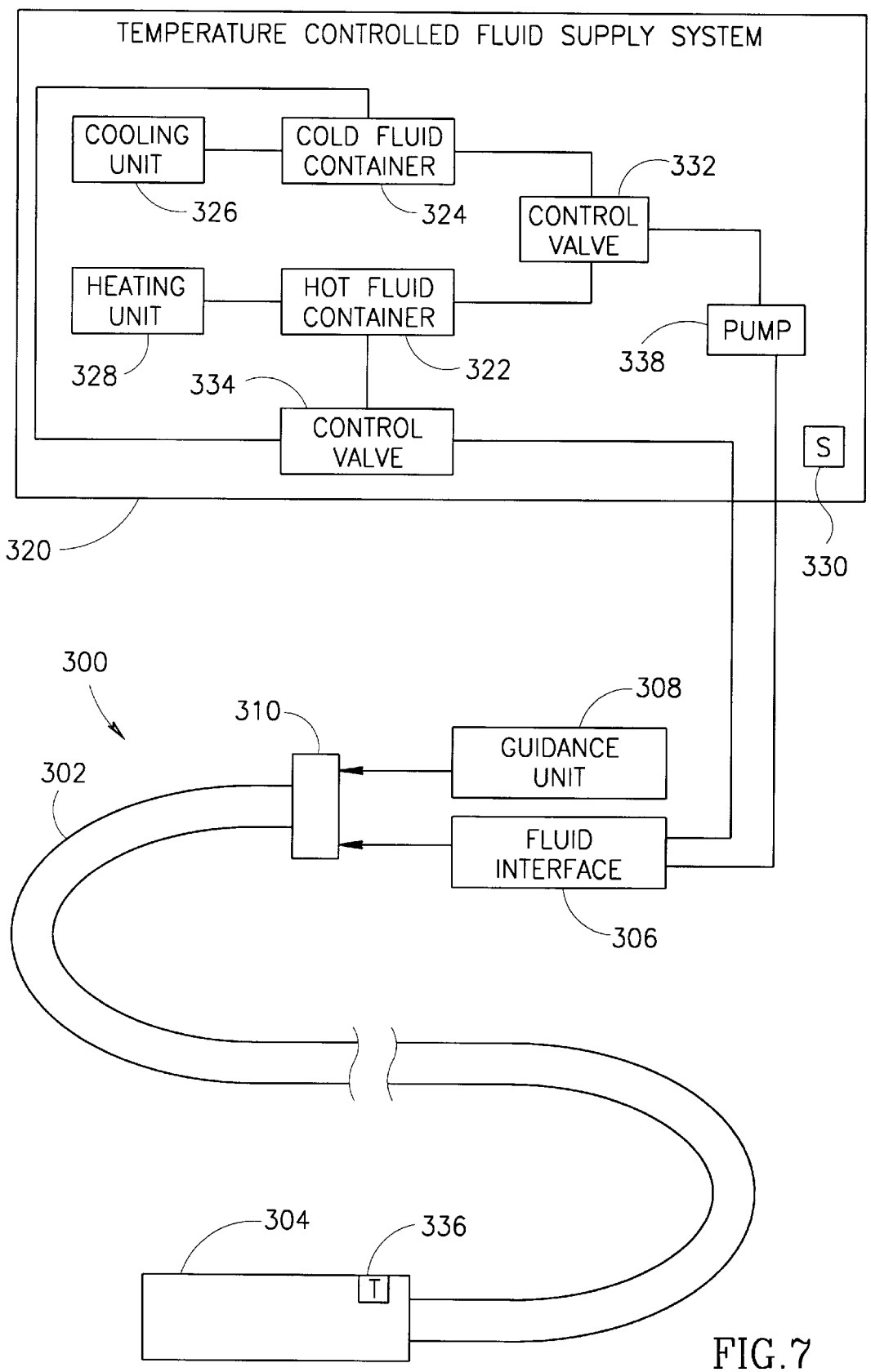
FIG. 7 is a schematic illustration of a system, constructed and operative in accordance with a further embodiment of the present invention.

Reference is now made to FIG. 7, which is a schematic illustration of a system, generally referenced 300, constructed and operative in accordance with a further embodiment of the present invention.

System 300 includes a catheter assembly 302, a guidance unit 308, a fluid connector 306 and a temperature control system 320.

The catheter assembly 302 includes a tip 304, a temperature sensor 336 for sensing the temperature of the treated area as well as the temperature of the tip 304 and a quick release interface 310. It is noted that the addition of temperature sensors is an option, provided by the invention. This addition enhances the control and accuracy of the temperature of the fluid and hence, the temperature of the SMA tip 304.

The guidance unit 308 enables the physician to guide the tip of the catheter 302, towards the target area to be treated.

The fluid connector 306 enables the physician to supply variable fluid temperature and flow into the catheter 302, and the like.

The temperature control system 320 provides a continuous supply of fluid according to the specification, received from the user via connector 306.

The temperature control system 320 includes a pump 338, a hot fluid container 322, a cold fluid container 324, a cooling unit 326, a heating unit 328, control valves 332 and 334 and a sensor 330.

The cooling unit 326 is connected to the cold fluid container 324. The hot fluid container 322, is connected to the heating unit 328 and to the control valves 332 and 334. The control valve 332 is connected between the pump 338 and both containers 324 and 322.

The pump 338 is further connected to the fluid connector 306, which is further connected to the control valve 334.

The cooling unit 326 cools the fluid which is contained in the cold fluid container 324. The heating unit 328 heats the fluid which is contained in the hot fluid container 322. The control valve 332 directs fluids received from the cold fluid container 324 and the hot fluid container 322 and provides the fluid to the pump 338.

The pump 338 provides a fluid at a controlled pressure to the fluid interface 306. This fluid flows towards the tip 304 thereby applying its temperature, thereon (i.e., when the temperature of the fluid is greater than the temperature of the tip, then the tip will be heated up and when the temperature of the fluid is lower than the temperature of the tip, then the tip will cool down).

After modifying the temperature of the tip 304, the fluid flows back to the temperature control system 320, via the fluid connector 306, to be stored in the containers. The control valve 334 provides fluid to the containers 322 and 324.

The fluid sensor 330 monitors the fluid at the output of the pump 338, thereby providing data relating to the temperature and pressure of the fluid. This data is used to control the pump 338 and the heating element 328 and the cooling element 326.

It is noted that the catheter assembly 302, can also conduct fluid, directly therethrough, and release it in the vicinity of the tip. Accordingly, the tip can be made of a wire which has a solid cross-section.

Figure 8:
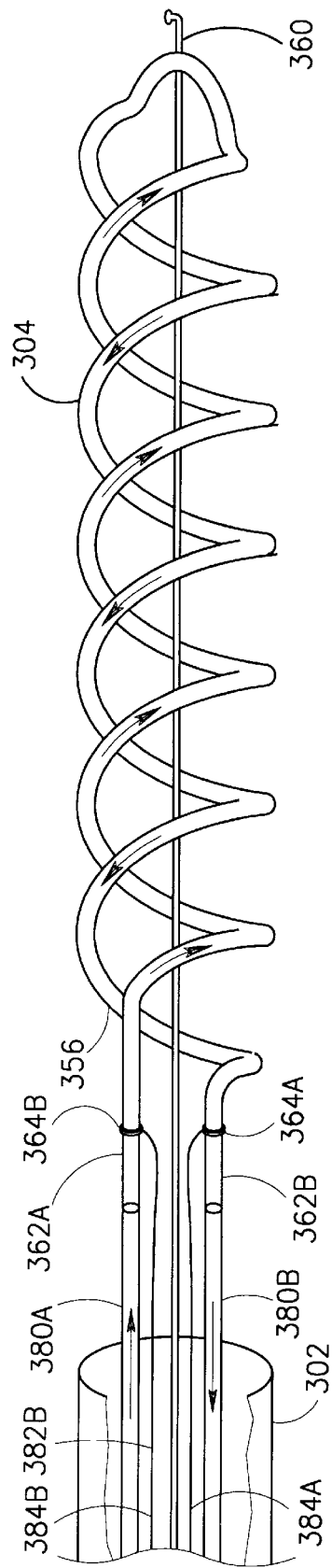
FIG. 8 is a schematic illustration in detail of the connection section of a helical SMA element and the inner side of the guiding catheter.

Reference is further made to FIG. 8, which is a schematic illustration in detail of the connection section of a helical SMA element 356 and the inner side of the guiding catheter 302 (FIG. 8). The helical SMA element 356 includes an inlet 362A and an outlet 362B, which are connected to a fluid inlet conduit 380A and a fluid outlet conduit 380B. The fluid inlet conduit 380A is connected to the inlet 362A, while the fluid outlet conduit 380B is connected to the outlet 362B. Temperature controlled fluid, provided by system 320, is provided to the helical SMA element 356 via the inlet fluid conduit 380A. After modifying the temperature of the helical SMA element 356, the fluid exits via the outlet fluid conduit 380B. It is noted that a guiding wire 360 is inserted through the guiding catheter 302 to the end of the tip 304.

According to the present example, the helical SMA element 356 is alternatively connected to two electrically conducting wires 384A and 384B, via electrical contacts 364A and 364B, respectively. These wires provide a flow of electrical current via the metal body of the helical SMA element 356, thereby heating it. According to this example, the heating is performed electrically, while the cooling can be performed either by setting the reduced diameter temperature to the body temperature of the patient or by introducing cooled fluid via conduits 380A and 380B.

Figure 9:
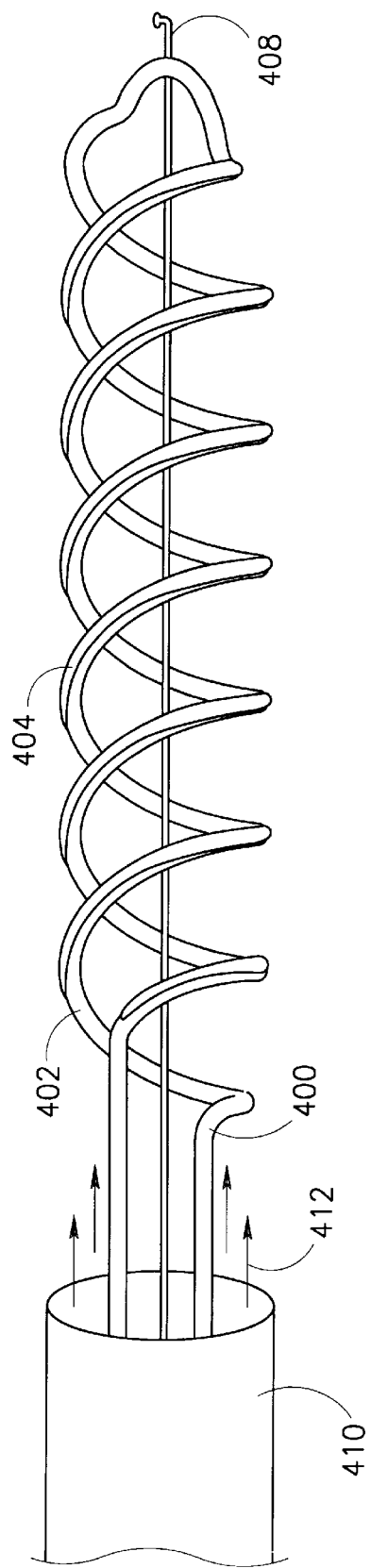
FIG. 9 is a schematic illustration in detail of a catheter tip, constructed and operative in accordance with another preferred embodiment of the present invention.

Reference is now made to FIGS. 9, 10A, 10B, 10C, 10D, 10E, 10F and 10G. FIG. 9 is a schematic illustration in detail of a catheter tip, generally referenced 400, constructed and operative in accordance with another preferred embodiment of the present invention. FIGS. 10A, 10B, 10C, 10D, 10E, 10F and 10G are illustrations of cross sectional variations for catheter tip 400, which include auxiliary elastic means.

Catheter tip 400 includes a helical SMA element 402, and a helical elastic element 404, attached thereto. SMA element 402 is generally similar to elements 104 and 304.

According to one aspect of the invention, the helical elastic element 404 is inserted within helical SMA element 402, as illustrated in FIGS. 10A, 10B, 10C, 10D and 10E. According to a further aspect of the invention (FIGS. 10F and 10G), the helical elastic element 404 is attached to the outer surface of helical SMA element 402.

Figure 10A:
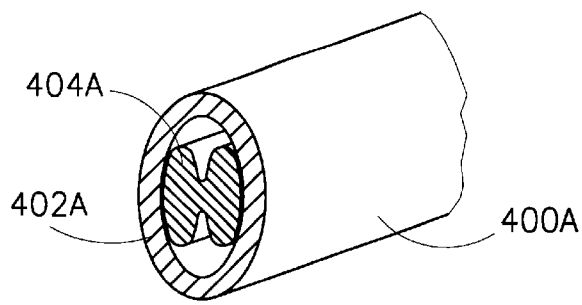
FIGS. 10A, 10B, 10C, 10D, 10E, 10F and 10G are illustrations of typical cross sectional variations for the catheter tip of FIG. 9.

FIG. 10A is a cross sectional illustration of a variation of SMA element 402, which includes a hollow helical SMA element 402A having an elliptic cross section and a helical elastic element 404B having an "I" cross section.

Figure 10B:
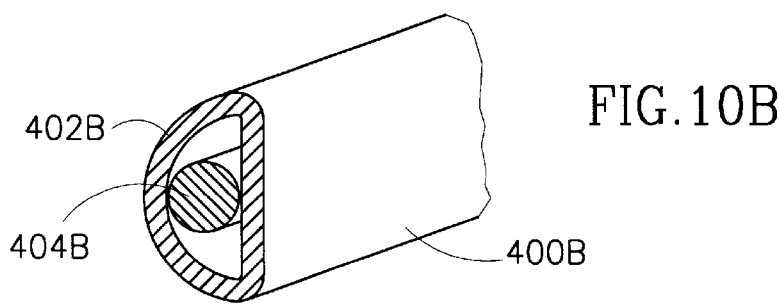

FIG. 10B is a cross sectional illustration of a variation of SMA element 402, which includes a hollow helical SMA element 402B having a semi-elliptic cross section and a helical elastic element 404B having a radial cross section.

Figure 10C:
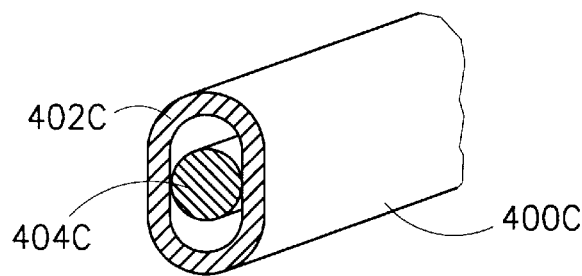

FIG. 10C is a cross sectional illustration of a variation of SMA element 402, which includes a hollow helical SMA element 402C having a near rectangle cross section and a helical elastic element 404C having a radial cross section.

Figure 10D:
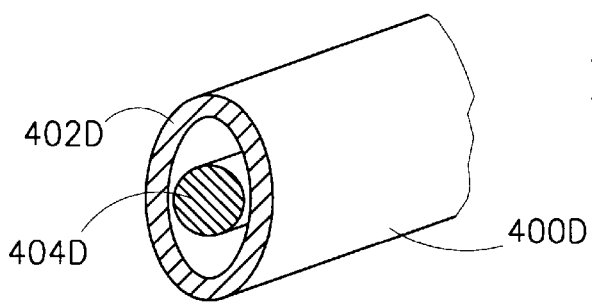

FIG. 10D is a cross sectional illustration of a variation of SMA element 402, which includes a hollow helical SMA element 402D having an elliptic cross section and a helical elastic element 404D having a radial cross section.

Figure 10E:
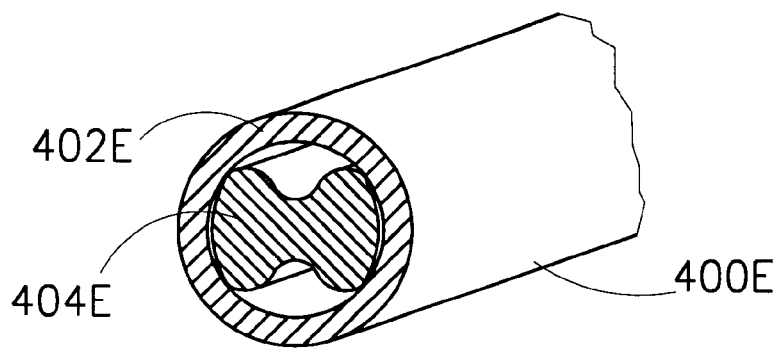

FIG. 10E is a cross sectional illustration of a variation of SMA element 402, which includes a hollow helical SMA element 402E having a radial cross section and a helical elastic element 404E having an "I" shaped cross section.

Figure 10F:
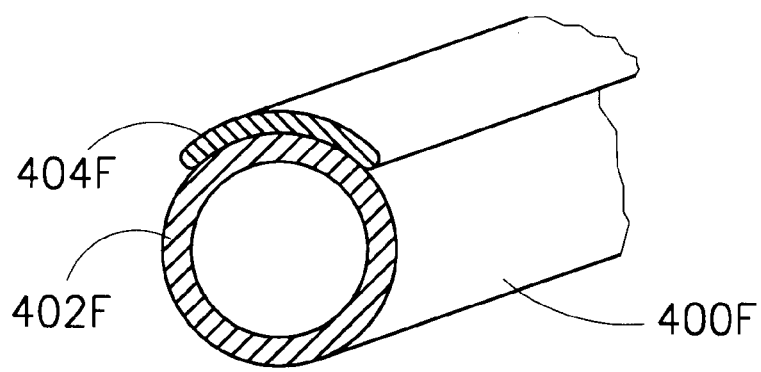

FIG. 10F is a cross sectional illustration of a variation of SMA element 402, which includes a hollow helical SMA element 402F having a radial cross section and an external elastic element 404F.

Figure 10G:
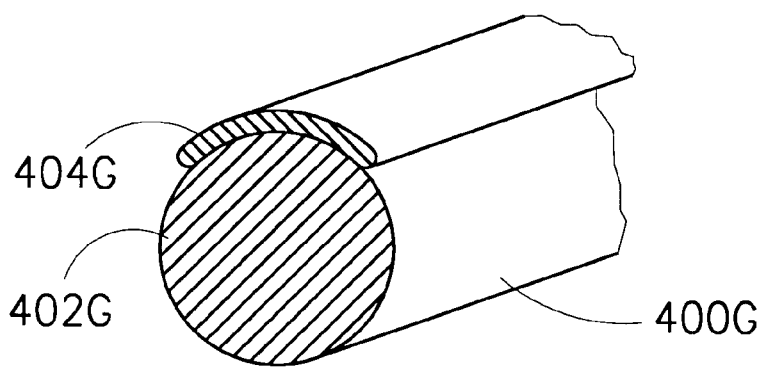

FIG. 10G is a cross sectional illustration of a variation of SMA element 402, which includes a solid (full) helical SMA element 402G having a radial cross section and an external elastic element 404G.

The helical SMA element 402 has a narrow circumference shape at a temperature which is equal to or lower than a first temperature value $T_1$. The helical SMA element 402 has a wide circumference shape at a temperature which is equal to or higher than a second temperature value $T_2$.

The helical elastic element 404 has a narrow diameter shape, which is in the order of the narrow diameter shape of the helical SMA element 402.

It is noted that the helical elastic element 404 can be deformed to a different shape, by an external force and return back by itself, to its original narrow circumference shape.

According to the present invention, the catheter tip 400 performs a transition from the narrow circumference shape to a wide circumference shape, by heating the helical SMA element 402 beyond predetermined temperature $T_2$. At this stage, the helical SMA element 402 is in an austenite state, where it applies force on helical elastic element 404, thereby deforming it into a shape which is generally the same shape of the helical SMA element 402 (i.e., a wide circumference).

At a later time, the catheter tip 400 performs a transition from the wide circumference shape, back to the narrow circumference shape, by cooling the helical SMA element 402 below predetermined temperature $T_1$.

Accordingly, the helical SMA element 402 transforms into a martensite state, where it becomes less rigid. Being in the martensite state, the helical SMA element 402 is no longer able to apply sufficient force onto helical elastic element 404. Hence, the helical elastic element 404, retracting to its initial shape, deforms the helical SMA element 402, into a shape which is generally the same initial shape of the helical elastic element 404 (i.e., a narrow circumference).

According to a further aspect of the invention, which is illustrated in FIG. 9, the temperature controlled fluid is provided through the guiding catheter 410 and released in the vicinity of the shape memory catheter tip. It is noted that the shape memory catheter tip can be cooled or heated, by this temperature controlled fluid, to temperatures other than the temperature of the environment in which the tip is placed. When the supply of temperature controlled fluid stops, then the shape memory catheter tip is either cooled or heated to this environment temperature.

Figure 11:
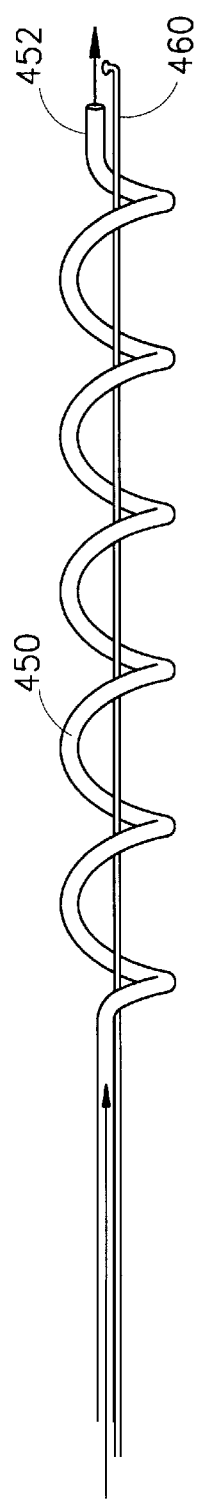
FIG. 11 is a schematic illustration of a catheter tip, constructed and operative in accordance with a further preferred embodiment of the present invention.

Reference is now made to FIG. 11, which is a schematic illustration of a catheter tip, generally referenced 450, constructed and operative in accordance with a further preferred embodiment of the present invention. Tip 450 is made of a hollow SMA tube which enables the flow of temperature controlled fluid therethrough. The tip 450 is inserted in the body of the patient over a guiding wire 460.

According to this aspect of the invention, one end tip 450 is opened. The temperature controlled fluid which is provided to the tip, travels through the tip 450 and is released through the tip end 452, in the vicinity of the shape memory catheter tip 450.

Figure 12:
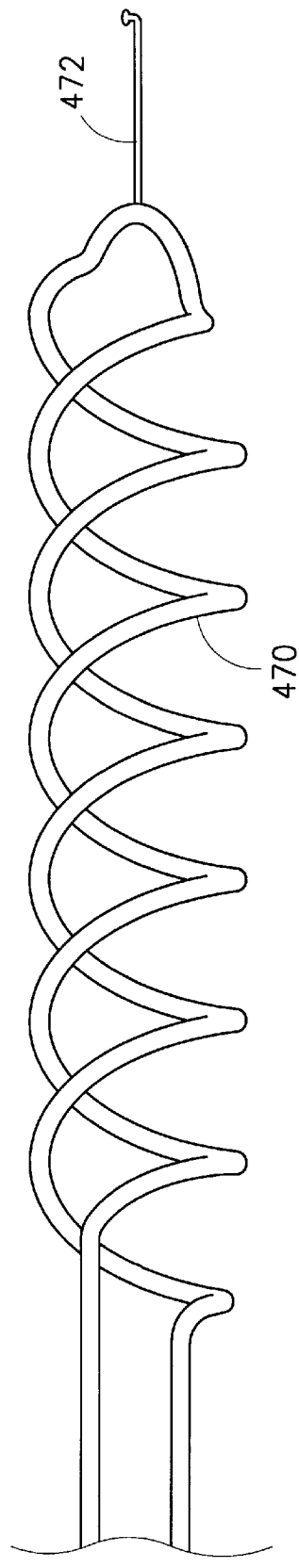
FIG. 12 is a schematic illustration of a catheter tip, constructed and operative in accordance with another preferred embodiment of the present invention.

Reference is now made to FIG. 12, which is a schematic illustration of a catheter tip, generally referenced 470, constructed and operative in accordance with another preferred embodiment of the present invention. shape memory catheter tip 470 includes a guiding tip 472, which extends at the front of the tip 470. The shape memory catheter tip 470 is guided in the tubular organ to its destination, using this guiding tip, without the requirement of a guiding wire. It is noted that a guiding wire can also be used as further guiding assistance.

It is noted that each part of a catheter, according to the invention, and especially the catheter tip, can be coated with an anti-coagulation material such as Heparin.

Figure 13:
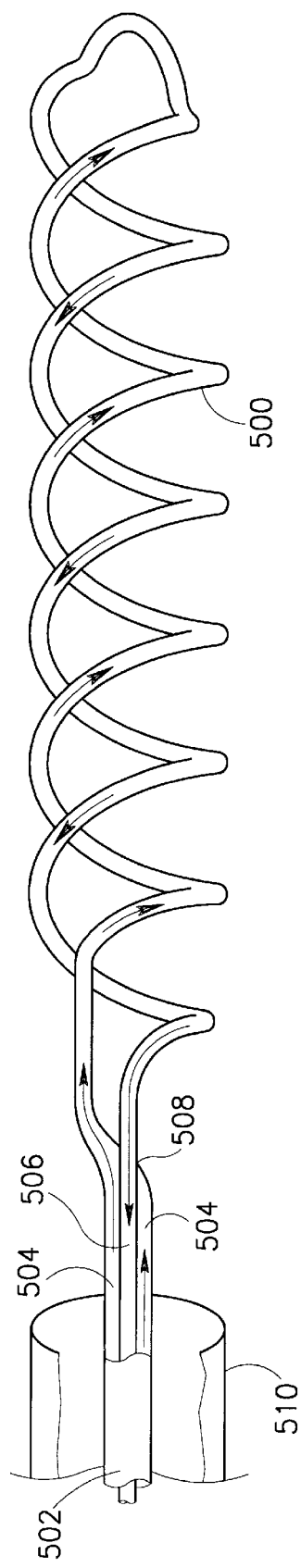
FIG. 13 is a schematic illustration of a catheter tip, and energy transfer means, constructed and operative in accordance with a further preferred embodiment of the present invention.

Reference is now made to FIG. 13, which is a schematic illustration of a catheter tip, generally referenced 500, and energy transfer means, generally referenced 502, constructed and operative in accordance with a further preferred embodiment of the present invention.

Energy transfer means include two concentric conduits 504 and 506, where conduit 504 is the outer conduit and conduit 506 is the inner conduit. The outer conduit 504 transfers the temperature controlled fluid to the tip 500 and the inner conduit 506 receives temperature controlled fluid from the tip and transfers it outside. It is noted that the directions of flow within the two conduits 504 and 506 can be swapped so that the inner conduit 506 transfers the temperature controlled fluid to the tip 500, while the outer conduit 504 transfers the temperature controlled fluid from the tip 500.

The entire assembly is generally inserted via a guiding catheter 510. It is noted that the concentric structure of the conduits provides reduced surface area and volume, so that a narrower guiding catheter can be used. Furthermore, the concentric structure provides a smoother shape, so that the movement of the conduits within the guiding catheter is easier.

It will be appreciated by persons skilled in the art that the present invention is not limited to what has been particularly shown and described hereinabove. Rather the scope of the present invention is defined only by the claims which follow.

What is claimed is:

1. A system for opening and temporarily supporting a portion of a generally tubular organ, comprising, in combination:

a dilation catheter including a shape memory catheter tip which is both (a) integral with said dilation catheter, and (b) incapable of being separated from said dilation catheter during times when the system functions according to its intended purposes, said shape memory catheter tip including a portion thereof which is formed of a shape memory alloy, means for insertion of the dilation catheter including said shape memory catheter tip at a first temperature into the generally tubular organ at a first desired location within said tubular organ, said shape memory catheter tip assuming a first shape at said first temperature, means for causing the temperature of said shape memory catheter tip to increase to a second temperature which is higher than said first temperature, thereby making said shape memory catheter tip to assume a second shape in response to the resulting rise in temperature; and elastic means integral with said shape memory catheter tip, wherein said elastic means has an initial shape, said initial shape is generally similar to said first shape, wherein said elastic means applies force on said shape memory catheter tip so as to deform said shape memory catheter tip toward said first shape.

2. The system according to claim 1, wherein said shape memory catheter tip is generally hollow, thereby enabling flow of bodily fluid therethrough.

3. The system according to claim 2, wherein said shape memory catheter tip enables flow of bodily fluid in a radial direction and in an axial direction.

4. The system according to claim 1, further comprising:

an energy control unit, connected to said dilation catheter, for controlling the temperature of said shape memory catheter tip; and an energy transfer unit, connected between said shape memory catheter tip and said energy control unit, and generally located within said dilating catheter, for transferring energy therebetween.

5. The system according to claim 4, wherein said energy transfer unit comprises at least one conduit, and
wherein said energy control unit comprises means for providing a temperature controlled fluid towards said shape memory catheter tip via said energy transfer unit.

6. The system according to claim 5, wherein one of said at least one conduit, is opened in the vicinity of said shape memory catheter tip, thereby releasing temperature controlled fluid in the vicinity of said shape memory catheter tip.

7. The system according to claim 5, wherein said shape memory catheter tip comprises a generally cylindrical coil, having a hollow cross section,
said generally cylindrical coil being connected to said at least one conduit at a first end, said generally cylindrical coil being open at a second end,
said at least one conduit transfers a temperature controlled fluid to said shape memory catheter tip, via said first end,
said shape memory catheter tip releasing said temperature controlled fluid via said second end.

8. The system according to claim 5, wherein said shape memory catheter tip comprises a generally cylindrical hollow coil, having an inlet and an outlet, and
wherein said energy transfer unit comprises two conduits,
wherein one of said two conduits is connected to said inlet for introducing said temperature controlled fluid thereto, and
wherein the other of said two conduits is connected to said outlet, for receiving said temperature controlled fluid therefrom.

9. The system according to claim 5, wherein said at least one conduit comprises two concentric conduits.

10. The system according to claim 3, wherein said energy transfer unit comprises an electricity conducting unit, connected electrically to said shape memory catheter tip, and
wherein said electricity conducting unit being further connected to an electric power supply unit.

11. The system according to claim 10, wherein said first temperature is equal or below the temperature of the environment, in which said shape memory catheter tip is placed.

12. The system according to claim 1, wherein said shape memory catheter tip comprises a generally cylindrical coil.

13. The system according to claim 12, wherein said first shape is generally the shape of a cylindrical coil having a first diameter and wherein said second shape is generally the shape of a cylindrical coil having a second diameter.

14. The system according to claim 13, wherein said first diameter is smaller than said second diameter.

15. The system according to claim 12, wherein said generally cylindrical coil is made of a solid cross section wire.

16. The system according to claim 12, wherein said generally cylindrical coil is made of a hollow cross section tube.

17. The system according to claim 12, wherein said generally cylindrical coil has a cross section, which is selected from the list consisting of:
radial cross section;
elliptical cross section;
semi radial cross section;
semi elliptical cross section, and
near rectangular cross section.

18. The system according to claim 1, wherein said shape memory alloy is selected from the list consisting of:

Ni—Ti;
Ni—Ti—X;
Cu—Ni—Al;
Cu—Zn—Al;
Fe—Mn—Si;
Ni—Ti—Co;
Ni—Cu—X; and
Ni—Al.

19. The system according to claim 1, wherein said second temperature is in the range of 38 degrees Celsius and 65 degrees Celsius.

20. The system according to claim 1, wherein said second temperature is in the range of 42 degrees Celsius and 50 degrees Celsius.

21. The system according to claim 1, wherein said first temperature is in the range of 5 degrees Celsius and 35 degrees Celsius.

22. The system according to claim 1, wherein said first temperature is in the range of 20 degrees Celsius and 32 degrees Celsius.

23. The system according to claim 1, wherein said elastic means are inserted within said shape memory catheter tip.

24. The system according to claim 1, wherein said elastic means are attached to said shape memory catheter tip.

25. The system according to claim 1, wherein a front section of said shape memory catheter tip is shaped as a guiding front end.

26. The system according to claim 1, further comprising guiding means having a guiding tip, wherein said guiding means is located within said dilation catheter and said guiding tip extends beyond said shape memory catheter tip.

27. The system according to claim 26, wherein said guiding tip is operable to move relative to said shape memory catheter tip.

28. A system for opening and temporarily supporting a portion of a generally tubular organ, comprising, in combination:
a dilation catheter for entering a generally tubular organ,
dilation means which is both (a) integral with said dilation catheter, and (b) incapable of being operationally separated from said dilation catheter for opening and temporarily supporting a potion of wall defining said tubular organ,
said dilation means including a shape memory catheter tip,
elastic means integral with said shape memory catheter tip, wherein said elastic means has an initial shape, said initial shape is generally similar to said first shape, wherein said elastic means applies force on said shape memory catheter tip so as to deform said shape memory catheter tip toward said first shape; and
means for causing a change in the temperature of said shape memory catheter tip from a first temperature to a second temperature, wherein said change in temperature causes the shape of said shape memory catheter tip to change, respectively, from a first shape to a second shape.

29. A system according to claim 28, wherein said dilating means is capable of supporting a portion of a generally tubular organ without requiring cessation of fluid flow through the organ at any time during use of the dilating means.

30. A method for opening and temporarily supporting a portion of a generally tubular organ, comprising the steps of:
a) causing the insertion of an integral catheter including a single lumen catheter tip of shape memory alloy at a first temperature value to be inserted into a generally tubular organ, b) positioning said shape memory catheter tip at a first desired location within said tubular organ, said shape memory catheter tip being both integral with said integral catheter and incapable of being separated from said integral catheter during the steps (a)–(f) herein, said shape memory catheter tip assuming a first shape at said first temperature value, c) causing the temperature of said shape memory catheter tip to change to a second temperature value which is different than said first temperature value, thereby facilitating said shape memory catheter tip to assume a second shape to support the portion of the generally tubular organ in response to the resulting change in temperature, d) maintaining said shape memory catheter tip at said first desired location for a desired period of time, e) thereafter causing the temperature of said shape memory catheter tip to change from said second temperature value to said first temperature value, and deforming said shape memory catheter tip by an elastic means thereby facilitating said shape memory catheter tip to assume a shape which is different from said second shape; and f) moving said integral catheter and shape memory catheter tip from said first desired location from said first desired location toward a second desired location or out of said generally tubular organ.

* * * * *